United States Patent [19]
Griswold

[11] Patent Number: 5,929,096
[45] Date of Patent: Jul. 27, 1999

[54] METHOD FOR TREATING ATOPIC DERMATITIS AND CONTACT DERMATITIS

[75] Inventor: Don Edgar Griswold, North Wales, Pa.

[73] Assignee: SmithKline Beecham Corporation, Philadelphia, Pa.

[21] Appl. No.: 08/913,003

[22] PCT Filed: Feb. 29, 1996

[86] PCT No.: PCT/US96/02950

§ 371 Date: Aug. 28, 1997

§ 102(e) Date: Aug. 28, 1997

[87] PCT Pub. No.: WO96/26725

PCT Pub. Date: Sep. 6, 1996

[51] Int. Cl.$^6$ .................................................. A61K 31/44
[52] U.S. Cl. ......................... 514/345; 514/343; 514/350; 514/354; 514/357; 514/358
[58] Field of Search ..................... 514/345, 354, 514/357, 358, 343, 350

[56] References Cited

FOREIGN PATENT DOCUMENTS

| | | |
|---|---|---|
| 9118601 | 12/1991 | WIPO . |
| WO 93/06085 | 4/1993 | WIPO . |
| WO 94/00437 | 1/1994 | WIPO . |

OTHER PUBLICATIONS

Journal of Investigative Dermatology, Ruzicka T. et al., Leukotrienes in skin of atopic dermatitis, vol. 82, No. 5 p. 563 dated May 5, 1994 (Abstract).

Allergy, 1900, vol. 45 pp. 457–463, S. Thorsen et al., Leukotriene $B_4$ in atopic dermatitis: increased skin levels and altered sensitivity of peripheral blood T–cells.

Yamashita et al., "Skin–Lightening Preparations Containing Fusaric Acid And/Or Picolinic Acids", *Chemical Abstracts*, 113:217815 (1990).

*Primary Examiner*—Phyllis G. Spivack
*Attorney, Agent, or Firm*—James M Kanagy; Charles M. Kinzig

[57] ABSTRACT

This invention relates to a method of treating atopic and contact dermatitis using compounds of formula (I)

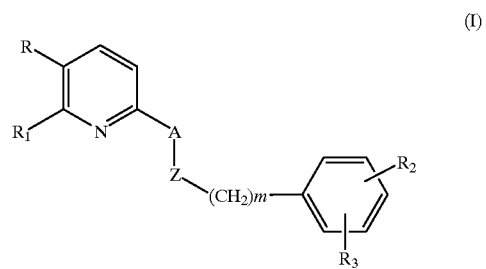

wherein the terms A, Z, R, $R_1$, $R_2$, $R_3$ and M are herein defined.

6 Claims, No Drawings

METHOD FOR TREATING ATOPIC DERMATITIS AND CONTACT DERMATITIS

This case is a 371 of PCT/US96/02950 filed Feb. 29, 1996.

SCOPE OF THE INVENTION

This invention relates to a method for treating atopic dermatitis or contact dermatitis comprising using certain compounds containing a substituted pyridyl group linked to a substituted phenyl group of an alkyl or heteroatom-containing tether.

BACKGROUND OF THE INVENTION

The family of bioactive lipids known as the eicosanoids exert pharmacological effects on cutaneous, respiratory, cardiovascular, and gastrointestinal systems. The leukotrienes are generally divided into two sub-classes, the peptidoleukotrienes (leukotrienes $C_4$, $D_4$ and $E_4$) and the dihydroxyleukotrienes (leukotriene $B_4$). This invention is primarily concerned with the hydroxyleukotrienes ($LTB_4$) but is not limited to this specific group of leukotrienes. In fact, the receptor with which $LTB_4$ interacts appears to also be utilized by a variety of other eicosanoids, including 12-HETE and dihydro 12-HETE. These receptors are either the same or closely-related so that compounds of this invention inhibit the action of several eicosanoids by antagonising this receptor.

These eicosanoids are derived from arachidonic acid and are critically involved in mediating many types of cardiovascular, pulmonary, dermatological, renal, allergic, and inflammatory diseases including asthma, adult respiratory distress syndrome, cystic fibrosis, psoriasis, and inflammatory bowel disease.

By antagonizing the effects of eicosanoids that interact at the $LTB_4$ receptor, or other pharmacologically active mediators at the end organ, for example airway smooth muscle, the compounds and pharmaceutical compositions of the present invention are valuable in the treatment of diseases in subjects, including human or animals, in which these eicosanoids are a factor.

SUMMARY OF THE INVENTION

This invention relates to a process for treating atopic dermatitis or contact dermatitis in a mammal which process comprises administering to a mammal suffering from either disease a therapeutically effective amount of at least one compound of formula I.

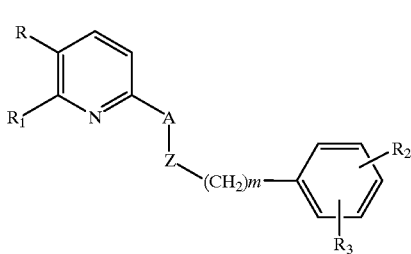

or an N-oxide, or a pharmaceutically acceptable salt thereof, where

A is $Ch_2$ and Z is $S(O)_q$ where q is 0, 1 or 2; CHOH; C=O; or $NR_x$; or O; or A is C=O and Z is $NR_x$;

m is 0–5;

R is $C_1$ to $C_{20}$-aliphatic, unsubstituted or substituted phenyl $C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O-, or R is unsubstituted or substituted phenyl $C_1$ to $C_{10}$-aliphatic-O- where substituted phenyl has one or more radicals selected from the group consisting of lower alkoxy, lower alkyl, trihalomethyl, and halo;

$R_1$ is —($C_1$ to $C_5$ aliphatic)$R_4$, —($C_1$ to $C_5$ aliphatic)CHO, —($C_1$ to $C_5$ aliphatic)$CH_2OR_8$, —$R_4$, —$CH_2OH$, or CHO;

$R_2$ is H, halo, lower alkyl, lower alkoxy, —CN, —$(CH_2)_n R_4$, —$CH(NH_2)(R_4)$, or —$(CH_2)_n R_9$ where n is 0–5 and where $R_9$ is —$N(R_7)_2$ where each $R_7$ is independently H, or an aliphatic group of 1 to 10 carbon atoms, or acyl of 1–6 carbon atoms, or a cycloalkyl—$(CH_2)_n$— group of 4 to 10 carbons where n is 0–3, or both $R_7$ groups from a ring which includes the nitrogen and having 4 to 6 carbons; or $R_3$ is hydrogen, lower alkyl, lower alkoxy, halo, —CN, $R_4$, $NHCONH_2$, or OH;

each $R_4$ group is independently —$COR_5$ where $R_5$ is —OH, a pharmaceutically acceptable ester-forming group —$OR_6$, or —OX where X is a pharmaceutically acceptable cation, or $R_5$ is —$N(R_7)_2$ where each $R_7$ is independently H, or an aliphatic group of 1 to 10 carbon atoms, or a cycloalkyl—$(CH_2)_n$— group of 4 to 10 carbons where n is 0–3, or both $R_7$ groups form a ring having 4 to 6 carbons, or $R_4$ is a sulfonamide, or an amide, or tetrazol-5-yl; and $R_8$ is hydrogen, $C_1$ to $C_6$ alkyl, or $C_1$ to $C_6$-acyl.

In another aspect, this invention relates to the use of a compound according to formula I in the manufacture of a pharmaceutical of a medicament for use in treating atopic dermatitis.

DETAILED DESCRIPTION OF THE INVENTION

The following definitions are used in describing this invention and setting out what the inventors believe to be their invention herein.

"Aliphatic" is intended to include saturated and unsaturated radicals. This includes normal and branched chains, saturated or mono or poly unsaturated chains where both double and triple bonds may be present in any combination. The phrase "lower alkyl" means an alkyl group of 1 to 6 carbon atoms in any isomeric form, but particularly the normal or linear form. "Lower alkoxy" means the group lower alkyl-O-. "Halo" means fluoro, chloro, bormo or iodo. "Acyl" means the radical having a terminal carbonyl carbon.

When reference is made to a substituted phenyl ring, it is meant that the ring can be substituted with one or more of the named substituents as may be compatible with chemical synthesis. Multiple substituents may be the same or different, such as where there are three chloro groups, or a combination of chloro and alkyl groups and further where this latter combination may have different alkyl radicals in the chloro/alkyl substituent pattern.

The phrase "a pharmaceutically acceptable ester-forming group" in $R_2$ and $R_3$ covers all esters which can be made from the acid function(s) which may be present in these compounds. The resultant esters will be ones which are acceptable in its application to a pharmaceutical use. By that it is meant that the mono or diesters will retain the biological activity of the parent compound and will not have an untoward or deleterious effect in their application and use in treating diseases. Such esters are, for example, those formed with one of the following radicals: $C_1$ to $C_6$ alkyl, phenyl $C_1$–$C_6$alkyl, cycloalkyl, aryl, arylalkyl, alkylaryl, alkylarylalkyl, aminoalkyl, indanyl, pivaloyloxymethyl, acetoxymethyl, propionyloxymethyl, glycyloxymethyl, phenylglycyloxymethyl, or thienylglycyloxymethyl. The most preferred ester-forming radicals are those where $R_3$ is alkyl, particularly alkyl of 1 to 10 carbons, (ie $CH_3$—$(CH_2)_n$— where n is 0–9), or phenyl—$(CH_2)_n$— where n is 0–4.

When $R_2$ is referred to as being an amine, that includes the radical —$NH_2$ and mono- or dialkylate derivatives of this —$NH_2$ radical. Preferred alkylated amines are the mono- or disubstituted amines having 1 to 6 carbons. When $R_2$ is referred to as being an amide, that includes all acylate derivatives of the $NH_2$ radical. The preferred amides are those having 1 to 6 carbons.

Where there is an acid group, amides may be formed. The most preferred amides are those where —$R_6$ is hydrogen or alkyl of 1 to 6 carbon atoms. Particularly preferred is the diethylamide or dimethylamide.

Pharmaceutically acceptable salts of the instant compounds are intended to be covered by this invention. These salts will be ones which are acceptable in their application to a pharmaceutical use. By that is meant that the salt will retain the biological activity of the parent compound and the salt will not have untoward or deleterious effects in its application and use in treating diseases.

Pharmaceutically acceptable salts are prepared in a standard manner, in a suitable solvent. The parent compound in a suitable solvent is reacted with an excess of an organic or inorganic acid, in the case of acid addition salts, or an excess of organic or inorganic base in the case where $R_4$ is OH.

N-oxides may also be prepared by means of selected oxidizing agents. These oxides are useful as intermediates in preparing the compounds of formula I and have useful pharmaceutical activity in and of themselves. Hence one can administer the N-oxides of formula I to a subject who is susceptible to or is suffering from a disease related to or caused by $LTB_4$ or similar eicosanoids which react at that receptor or similar receptor.

If by some combination of substituents, a chiral center is created or another form of an isomeric center is created in a compound of this invention, all forms of such isomer(s) are intended to be covered herein. These compounds may be used as a racemic mixture or the racemates may be separated and the individual enantiomer used alone. Olefins may have the cis or trans configuration (E or Z); either are useful in the practice of this invention.

As LTB4 receptor antagonists, these compounds can be used in treating a variety of disease associated with or attributing their origin or affect to leukotrienes and related eicosanoids, particularly $LTB_4$. Thus it is expected that these compounds can be used to treat allergic diseases such of a pulmonary and non-pulmonary nature. For example these compounds will be useful in antigen-induced anaphylaxis; for treating asthma and allergic rhinitis; psoriasis, or irritable bowel disease; ocular diseases such as uveitis, and allergic conjunctivitis.

The preferred compounds are those where Z is O or $S(O)_q$; m is 0–3; n is 0–2; R is alkoxy of 8 to 15 carbon atoms or unsubstituted or substituted pheny-$C_1$ to $C_{10}$-aliphatic-O-; and $R_1$ is —($C_1$ to $C_5$ aliphatic)$R_4$ or —($C_1$ to $C_5$-aliphatic)$CH_2OR_8$. The more preferred compounds of this invention are those where $R_1$ is $R_4CH=CH$— and $R_2$ is —$COR_5$ or —$NHSO_2CF_3$. Another set of preferred compounds are the anilines, those where $R_2$ is $N(R_7)_2$, particularly where $R_7$ is hydrogen. A third set of preferred compounds are those where both $R_2$ and $R_3$ are hydrogen. Yet another set of preferred compounds are the 2,6-dihalophenyl analogs, particularly the 2,6-dichlorophenyl compounds.

The illustrated compounds

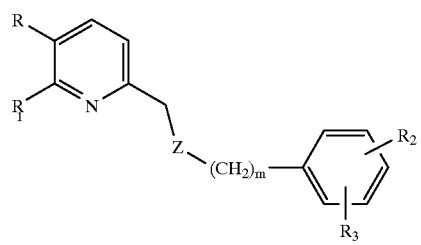

I

| Z—$(CH_2)_m$— | R | $R_1$ | $R_2$ |
|---|---|---|---|
| S (m is 0) | $H_{25}C_{12}$—O— | *HOOC—CH=CH— | m-COOH |
| S (m is 0) | $H_{25}C_{12}$—O— | *HOOC—CH=CH— | p-COOH |
| S (m is 0) | $H_{25}C_{12}$—O— | *HOOC—CH=CH— | o-COOH |
| S=O (m is 0) | $H_{25}C_{12}$—O— | *HOOC—CH=CH— | m-COOH |
| S=O (m is 0) | $H_{25}C_{12}$—O— | *HOOC—CH=CH— | p-COOH |
| S=O (m is 0) | $H_{25}C_{12}$—O— | *HOOC—CH=CH— | o-COOH |
| $SO_2$ (m is 0) | $H_{25}C_{12}$—O— | *HOOC—CH=CH— | m-COOH |
| O (m is 0) | $H_{25}C_{12}$—O— | *HOOC—CH=CH— | m-COOH |
| O (m is 0) [N-oxide] | $CH_3O$—Ph—$(CH_2)_8$—O— | *HOOC—CH=CH— | m-COOH |
| O (m is 0) [N-oxide] | $H_{25}C_{12}$—O— | *HOOC—CH=CH— | m-COOH |

*Trans configuration.

In addition, the following named compounds are illustrated herein:

1-fluoro-3-[2-thia-3-[2-(E-2-carboxyethenyl)-3-[4-(4-methoxyphenyl)butyloxy]-6-pyridyl]propyl]benzene, lithium salt;

3-[2-thia-3-[2-(E-2-carboxyethenyl)-3-[4-(4-methoxyphenyl)butyloxy]-6-pyridyl]propyl]benzene, lithium salt;

3-[2-thia-3-[2-(2-carboxyethanyl)-3-[4-(4-methoxyphenyl)butyloxy[-6-pyridyl]propyl]benzene, lithium salt;

2-[2-thia-3-[2-(2-carboxyethenyl)-3-[4-(4-methoxyphenyl)butyloxy]-6-pyridyl]ethyl]benzene, lithium salt;

1-fluoro-4-[2-thia-3-[2-(2-carboxyethanyl)-3-[4-(4-methoxyphenyl)butyloxy]-6-pyridyl]propyl]benzene, lithium salt;

1-fluoro-4-[2-thia-3-[2-(E-2-carboxyethenyl)-3-[4-(4-methoxyphenyl)butyloxy]-6-pyridyl]propyl]benzene, lithium salt;

3-[1-thia-2-[2-(E-2-carboxyethenyl)-3-[8-(4-methoxyphenyl)octyloxy]-6-pyridyl]ethyl]benzoic acid, 3-[1-oxythia-2-[2-(E-2-carboxyethenyl)-3-[-(4-methoxyphenyl)octyloxy]-6-pyridyl]ethyl]benzoic acid, 3-[1-thia-2-(E-2-carboxyethenyl)-3-dodecyloxy-6-pyridyl]ethyl]benzoic acid, 3-[1-oxythia-2-[2-(E-2-carboxyethenyl)-3-dodecyloxy-6-pyridyl]ethyl]benzoic acid, 3-[1-dioxythia-2-[2-(E-2-carboxyethenyl)-3-dodecyloxy-6-pyridyl]ethyl]benzoic acid, 2-[1-oxythia-2-[2-(E-2-carboxyethenyl)-3-dodecyloxy-6-pyridyl]ethyl]benzoic acid, lithium salt N-[3-[1-thia-2-[2-(E-2-carboxyethenyl)-3-dodecyloxy-6-pyridyl]ethyl]-phenyl]trifluoromethanesulfonamide, N-[3-[1-thia-2-[2-(E-2-carboxyethenyl)-3-(8-(4-methoxyphenyl)octyloxy)-6-pyridyl]ethyl]phenyl] trifluoromethanesulfonamide, N-[3-[1-oxythia-2-[2-(E-2-carboxyethenyl)-3-(8-(4-methoxyphenyl)octyloxy)-6-pyridyl]ethyl]phenyl]-trifluoromethanesulfonamide, N-[3-[1-oxythia-2-[2-(E-2-carboxyethenyl)-3-(8-(4-methoxyphenyl)octyloxy)-6-pyridyl]ethyl]phenyl]-phenylsulfonamide, N-[3-[1-thia-2-[2-(E-2-carboxyethenyl)-3-(8-(4-methoxyphenyl)octyloxy)-6-pyridyl]ethyl]-phenyl] phenylsulfonamide, 3-[1-oxa-2-[2-(E-2-carboxyethenyl)-3-dodecyloxy-6-pyridyl]ethyl]benzoic acid, 3-[1-oxa-2-[2-(E-2-carboxyethenyl)-3-[8-(4-methoxyphenyl)octyloxy]-6-pyridyl]ethyl]benzoic acid, 3-[1-oxa-2-[2-(E-2-carboxyethenyl)-3-[8-(4-methoxyphenyl)octan-1-yl]-6-pyridyl]ethyl]benzoic acid, 4-[2-thia-3-[2-(E-2-carboxyethenyl)-3-[8-(4-methoxyphenyl)octyloxy]-6-pyridyl]propyl]benzoic acid, 4-[2-thia-3-[2-(E-2-carboxyethenyl)-3-[4-(4-methoxyphenyl)butyloxy]-6pyridyl]propyl]benzoic acid, 3-[2-thia-3-[2-(E-2-carboxyethenyl)-3-[8-(4-methoxyphenyl)octyloxy]-6-pyridyl]propyl]benzoic acid, 3-[2-thia-3-[2-(E-2-carboxyethenyl)-3-[4-(4-methoxyphenyl)butyloxy]-6-pyridyl]propyl]benzoic acid, 3-[2-thia-3-[2-(2-carboxyethanyl)-3-[8-(4-methoxyphenyl)octyloxy]-6-pyridyl]propyl]benzoic acid, 3-[2-thia-3-[2-(E-2-carboxyethenyl)-3-(8-(4-methoxyphenyl)octyloxy)-6-pyridyl]propyl]-N,N,-dimethylbenzamide, lithium salt 3-[2-thia-3-[2-(E-2-carboxyethenyl)-3-(4-(4-methoxyphenyl)butyloxy)-6-pyridyl]propyl]-N,N-dimethylbenzamide, lithium salt, 3-[2-thia-3-[2-(E-2-carboxyethenyl)-3-[4-phenylbutyloxy]-6-pyridyl]propyl]benzoic acid, 3-[2-thia-3-[2-(E-2-carboxyethenyl)-3-[8-phenyloctyloxy]-6-pyridyl]propyl]benzoic acid, 3-[2-thia-3-[2-(2-carboxyethanyl)-3-[4-(4-methoxyphenyl)butyloxy]-6-pyridyl]propyl]benzoic acid, 4-[2-thia-3-[2-(E-2-carboxyethenyl)-3-[8-(4-methoxyphenyl)octyloxy]-6-pyridyl]propyl]phenylacetic acid, 4-[2-oxythia-3-[2-(E-2-carboxyethenyl)-3-[8-(4-methoxyphenyl)octyloxy]-6-pyridyl]propyl]benzoic acid, 3-[2-oxythia-3-[2-(E-2-carboxyethenyl)-3-[8-(4-methoxyphenyl)octyloxy]-6-pyridyl]propyl]benzoic acid, 4-[2-oxythia-3-[2-(E-2-carboxyethenyl)-3-[8-(4-methoxyphenyl)octyloxy]-6-pyridyl]propyl]phenylacetic acid, 3-[2-dioxythia-3-[2-(E-2-carboxyethenyl)-3-[8-(4-methoxyphenyl)octyloxy]-6-pyridyl]propyl]benzoic acid, 5-[3-[2-thia-3-[2-(E-2-carboxyethenyl)-3-[8-(4-methoxyphenyl)octyloxy]-6-pyridyl]propyl]phenyl] tetrazole, 3-[1-oxa-2-[2-(E-2-carboxyethenyl)-3-(8-(4-methoxyphenyl)octyloxy)-6-pyridyl]ethyl]aniline, 5-carboxy-3-[1-oxa-2-[2-(E-2-carboxyethenyl)-3-(8-(4-methoxyphenyl)octyloxy)-6-pyridyl]ethyl]aniline, 3-[1-thia-2-[2-(E-2-carboxyethenyl)-3-(8-(4-methoxyphenyl)octyloxy)-6-pyridyl]ethyl]aniline, 3-[1-thia-2-[2-(E-2-carboxyethenyl)-3-(8-(4-trifluoromethylphenyl)octyloxy) -6-pyridyl]ethyl]aniline, 3-[1-oxythia-2-[2-(E-2-carboxyethenyl)-3-(8-(4trifluoromethylphenyl)octyloxy)-6-pyridyl]ethyl] aniline, lithium salt 3-[1-thia-2-[2-(E-2-carboxyethenyl)-3-(8-phenyloctyloxy)-6-pyridyl]ethyl]aniline, lithium salt 3-[1-oxythia-2-[2-(E-2-carboxyethenyl)-3-(8-(4-fluorophenyl)octyloxy)-6-pyridyl]ethyl]aniline, 3-[1-oxythia-2-[2-(E-2-carboxyethenyl)-3-(8-phenyl) octyloxy)-6-pyridyl]ethyl]aniline, 3-[1-thia-2-[2-(E-2-carboxyethenyl)-3-(8-(4-methoxyphenyl)octyloxy)-6-pyridyl]ethyl]-N,N-dimethylaniline, 3-[1-thia-2-[2-(E-2-carboxyethenyl)-3-(4-(4-methoxyphenyl)butyloxy)-6-pyridyl]ethyl]aniline, lithium salt 3-[1-oxythia-2-[2-(E-2-carboxyethenyl)-3-(4-(4-methoxyphenyl)butyloxy)-6-pyridyl]ethyl]aniline, lithium salt 3-[1-dioxythia-2-[2-(E-2-carboxyethenyl)-3-(4-(4-methoxyphenyl)butyloxy)-6-pyridyl]ethyl]aniline, lithium salt 3-[2-thia-3-[2-(E-2-carboxyethenyl)-3-(8-(4-methoxyphenyl)octyloxy)-6-pyridyl]ethyl]-N,N-dimethylaniline, 3-[1-oxythia-2-[2-(E-2-carboxyethenyl)-3-(8-(4-methoxyphenyl)octyloxy)-6-pyridyl]ethyl]aniline, 3-[1-oxythia-2-[2-(E-2-carboxyethenyl)-3-(8-(4-methoxyphenyl)octyloxy)-6-pyridyl]ethyl]-N,N-dimethylaniline, 3-[1-dioxythia-2-[2-(E-2-carboxyethenyl)-3-(8-(4-methoxyphenyl)octyloxy)-6-pyridyl]ethyl]aniline, (E)-lithium 3-[3-[4-(4-methoxyphenyl)butyloxy]-6-[(2-phenylthio)methyl]-2pyridinyl]-2-propenoate, (E)-lithium 3-[3-[4-(4-methoxyphenyl)butyloxy]-6-[(3,4-dichlorophenylthio)methyl]-2-pyridinyl]-2-propenoate, (E)-lithium 3-[3-[4-(4-methoxyphenyl)butyloxy]-6-[(4-chlorophenylthio)methyl]-2-pyridinyl]-2-propenoate, (E)-sodium 3-[3-[4-(4-methoxyphenyl)butyloxy]-6-[(4-fluorophenylthio)methyl]-2-pyridinyl]-2-propenoate, (E)-lithium 3-[3-[4-(4-methoxyphenyl)butyloxy]-6-[(2-chlorophenylthio)methyl]-2-pyridinyl-2-propenoate, (E)-sodium 3-[3-[4-(4-methoxyphenyl)butyloxy]-6-[(2-chlorobenzylthio)methyl]-2-pyridinyl]-2-propenoate,
(E)-sodium 3-[3-[4-(4-methoxyphenyl)butyloxy]-6-[(2-methylphenylthio)methyl]-2-pyridinyl]-2-propenoate,
(E)-sodium 3-[3-[4-(4-methoxyphenyl)butyloxy]-6-[(3-chlorophenylthio)methyl]-2-pyridinyl]-2-propenoate,
(E)-sodium 3-[3-[4-(4-methoxyphenyl)butyloxy]-6-[(2-methoxyphenylthio)methyl]-2-pyridinyl]-2-propenoate,
(E)-sodium 3-[3-[4-(4-methoxyphenyl)butyloxy]-6-[(2,4-dichlorophenylthio)methyl]-2-pyridinyl]-2-propenoate,
(E)-sodium 3-[3-[4-(4-methoxyphenyl)butyloxy]-6-[(2-bromophenylthio)methyl]-2-pyridinyl]-2-propenoate,
(E)-sodium 3-[3-[4-(4-methoxyphenyl)butyloxy]-6-[(2-methylphenylthio)methyl]-2-pyridinyl]-2-propenoate,
(E)-sodium 3-[3-[4-(4-methoxyphenyl)butyloxy]-6-[(2,6-fluorophenylthio)methyl]-2-pyridinyl]-2-propenoate,
(E)-sodium 3-[3-[4-(4-methoxyphenyl)butyloxy]-6-[(2,6-dimethylphenylthio)methyl]-2-pyridinyl]-2-propenoate,
(E)-sodium 3-[3-[4-(4-methoxyphenyl)butyloxy]-6-[(2,6-dimethoxyphenylthio)methyl]-2-pyridinyl]-2-propenoate,
(E)-lithium 3-[3-[4-(4-methoxyphenyl)butyloxy]-6-[(2,6-dichlorophenylthio)methyl]-2-pyridinyl]-2-propenoate,
(E)-sodium 3-[3-[4-(4-fluorophenyl)butyloxy]-6-[(2,6-dichlorophenylthio)methyl]-2-pyridinyl]-2-propenoate,
(E)-sodium 3-[3-[4-(4-fluorophenyl)butyloxy]-6-[(2,6-difluorophenylthio)methyl]-2-pyridinyl]-2-propenoate,
(E)-sodium 3-[3-[2-(4-fluorophenyl)ethyloxy]-6-[(2,6-dichlorophenylthio)methyl]-2-pyridinyl]-2-propenoate,
(E)-sodium 3-[3-[2-(4-fluorophenyl)ethyloxy]-6-[(2,6-difluorophenylthio)methyl]-2-pyridinyl]-2-propenoate,
(E)-sodium 3-[3-(4-fluorobenzyloxy)-6-[(2,6-dichlorophenylthio)methyl]-2-pyridinyl]-2-propenoate,
(E)-sodium 3-[3-[4-phenylbutyloxy]-6-[(2,6-dichlorophenylthio)methyl]-2-pyridinyl]-2-propenoate,
(E)-sodium 3-[3-[2-phenylethyloxy]-6-[(2,6-dichlorophenylthio)methyl]-2-pyridinyl]-2-propenoate,
(E)-sodium 3-[3-[2-(4-fluorophenyl)ethyloxy]-6-[(2,6-dichlorophenylthio)methyl]-2-pyridinyl]-2-propanoate,
(E)-sodium 3-[3-[4-(4-fluorophenyl)butyloxy]-6-[(2,6-dichlorophenylthio)methyl]-2-pyridinyl]-2-propanoate,
(E)-sodium 3-[3-[4-(4-methoxyphenyl)butyloxy]-6-[(2,6-dichlorophenylthio)methyl]-2-pyridinyl]-2-propanoate,
(E)-sodium 3-[3-[2-(4-methoxyphenyl)ethyloxy]-6-[(2,6-dichlorophenylthio)methyl]-2-pyridinyl]-2-propenoate,
(E)-sodium 3-[3-[2-(4-fluorophenyl)ethyloxy]-6-[(2,4,6-trichlorophenylthio)methyl]-2-pyridinyl]-2-propenoate,
(E)-sodium 3-[3-[2-(4-fluorophenyl)ethyloxy]-6-[(2-chloro-6-methylphenylthio)methyl]-2-pyridinyl]-2-propenoate,
(E)-sodium 3-[3-[2-(4-methoxyphenyl)ethyloxy]-6-[(2,6-dichlorophenylthio)methyl]-2-pyridinyl]-2-propanoate,
(E)-3-[3-[2-(4-chlorophenyl)ethyloxy]-6-[(2,6-dichlorophenylthio)methyl]-2-pyridinyl]-2-propenoic acid,
(E)-3-[3-[8-(4-methoxyphenyl)octyloxy]-6-[(2,6-dichlorophenylthio)methyl]-2-pyridinyl]-2-propenoic acid,
(E)-3-[3-[2-phenethyloxy]-6-[(2,6-dichlorophenylthio)methyl]-2-pyridinyl]-2-propenoic acid,
(E)-3-[3-[3-phenylpropyloxy]-6-[(2,6-dichlorophenylthio)methyl]-2-pyridinyl]-2-propenoic acid,
(E)-N,N-diethyl 3-[3-[2-phenethyloxy]-6-[(2,6-dichlorophenylthio)methyl]-2-pyridinyl]-2-propenamide,
(E)-3-[3-[2-phenethyloxy]-6-[(2,6-dichlorophenyloxy)methyl]-2-pyridinyl]-2-propenoic acid,
(E)-3-[3-[2-(thien-2-yl)ethyloxy]-6-[(2,6-dichlorophenylthio)methyl]-2-pyridinyl]-2-propenoic acid,
(E)-3-[3-[2-(thien-3-yl)ethyloxy]-6-[(2,6-dichlorophenylthio)methyl]-2-pyridinyl]-2-propenoic acid,
(E)-3-[3-[2-(3-methylthiazol-2-yl)ethyloxy]-6-[(2,6-dichlorophenylthio)methyl]-2-pyridinyl]-2-propenoic acid,
(E)-N,N-diethyl 3-[3-[2-phenethyloxy]-6-[(2,6-dichlorophenylthio)methyl]-2-pyridinyl]-2-propenamide,
(E)-3-[3-[2-phenethyloxy]-6-[(2,6-dichlorophenylsulfinyl)methyl]-2-pyridinyl]-2-propenoic acid,
(E)-3-[3-[2-phenethyloxy]-6-[(2,6-dichlorophenylsulfonyl)methyl]-2-pyridinyl]-2-propenoic acid,
3-[3-[2-phenethyloxy]-6-[(2,6-dichlorophenylthio)methyl]-2-pyridinyl]propanoic acid,
3-[3-[2-phenethyloxy]-6-[(2,6-dichlorophenylsulfinyl)methyl]-2-pyridinyl]propanoic acid,
3-[3-[2-phenethyloxy]-6-[(2,6-dichlorophenylsulfonyl)methyl]-2-pyridinyl]propanoic acid,
3-[3-[8-(4-methoxyphenyl)octyloxy]-6-[(2,6-dichlorophenylsulfinyl)methyl]-2-pyridinyl]propanoic acid,
3-[3-[8-(4-methoxyphenyl)octyloxy]-6-[(2,6-dichlorophenyldioxysulfonyl)methyl]-2-pyridinyl]propanoic acid, or
a free acid thereof or another pharmaceutically acceptable salt.

Synthesis

The compounds of this invention can be made by the methods published in several patent applications, including but not limited to copending U.S. application Ser. No. 08/211,063 filed 18 Jul. 1994 and prior published as PCT/US92/07466 (WO93/06085) and copending U.S. application Ser. No. 08/163,974 filed 08 Dec. 1993 and prior published as PCT application Ser. No. PCT/US93/06234 (WO94/00437).

As disclosed in the aforementioned publications there are several methods for preparing these compounds. One generic process comprises preparing a 6-(halomethyl)pyridyl adduct and then condensing this fragment with the appropriate mercaptan or alcohol to make compounds where Z is sulfur or oxygen. Usually, functional groups such as acid groups will be protected; any acid group may be derivatized in some manner to render it unreactive. After the condensation reaction, protecting groups may be removed to provide the parent functionality, e.g. an acid. Further modification of these reactive groups can then be carried out, such as forming a salt, an amide, an ester or the like. Sulfonamides are prepared from the corresponding amines by literature methods. Tetrazoles are prepared from the corresponding acid halide, e.g., the acid chloride, by literature methods.

More specific illustrations of chemistry for making these compounds is provided in the following reaction schemes. Scheme I outlines a means for making a substituted phenylalkyl tail which is R.

Scheme I

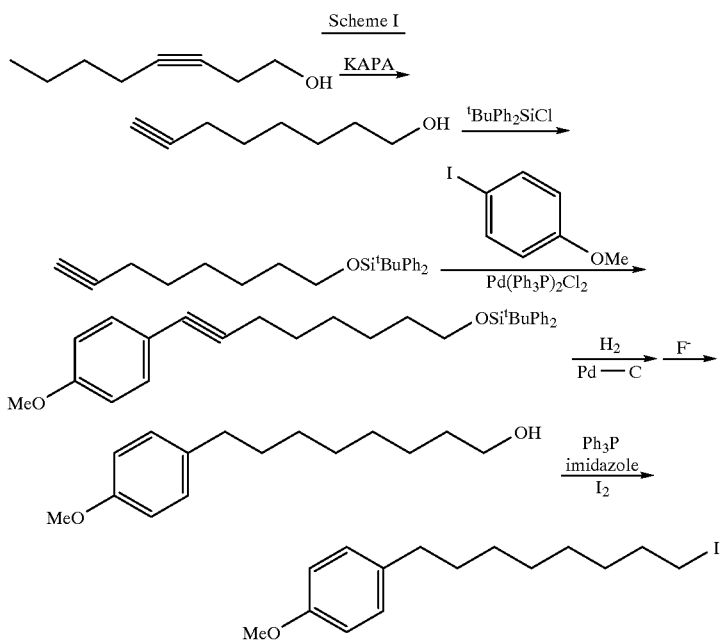

The starting alcohol, represented here as the 3-octyn-1-ol, is commercially available (Lancaster Synthesis). To migrate the triple bond to the ω-carbon, KH and 1,3-diaminopropane are combined and stirred to a homogeneous mix. This can be done at ambient temperature or thereabouts. This mix is then cooled, preferably to about 0° C. or thereabouts, whereupon the alcohol is added. Stirring is then commenced at about room temperature for 15 to 20 hours or so. Water is added to quench the reaction and the produce is recovered.

Protecting the alcohol is accomplished by forming a silyl ether illustrated here as the t-butyldiphenylsilyl ether. Other silyl ethers could be used. The alcohol is dissolved in a polar solvent, for example dimethylformamide, and imidazole is added followed by the desired silane. All this is carried out under an inert atmosphere such as argon. Ambient temperature is acceptable for effecting the reaction.

Adding the phenyl group is done in a dry environment using an amine for a solvent and an inert atmosphere. To a flask containing a solvent such as triethylamine under argon is added the silylether followed by a halophenyl compound, eg. iodoanisole, a palladium catalyst $(Ph_3P)_2PdCl_2$ and CuI, both of the latter in catalytic amounts. Heat is used to effect the reaction, usually a temperature of up to about 50° C. will be sufficient. Two or more hours, up to six but often about four at the elevated temperature will usually cause the reaction to go to completion.

The triple bond is then saturated, preferably by catalytic hydrogenation. For example, the silyl ether can be dissolved in a saturated solvent such as an alcohol, a heavy metal catalyst added (Pd-C) and the mixture put under $H_2$ for a time sufficient to reduce the triple bond. Stirring for 2 to 6 hours will usually effect the reaction.

Recovering the alcohol is done by treating the silyl ether with a fluoride source such as tetrabutylammonium fluoride. Reactants are combined at a mildly reduced temperature, eg. 0° C., then the reaction is allowed to run its course at ambient temperature or there about. Several hours may be needed for the reaction to go to completion. Produce was recovered by extraction means.

Converting the alcohol to the iodo compound is accomplished using a phosphine, imidazole and $I_2$. In actual practice, this transformation is accomplished by adding to a solution of alcohol under argon, a molar excess of triphenylphosphine, for example, and a three-fold excess of imidazole followed by iodine. Materials are combined at room temperature, but then the reaction pot may be heated to between 50–70° C. for a brief period, 10 minutes to an hour to complete the reaction. Standard procedures are then used to recover and purify the product.

Scheme II illustrates an alternative process for making R groups.

Scheme II

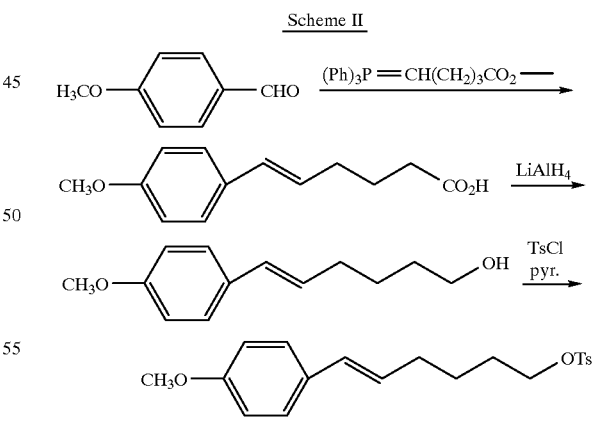

While the methoxyphenyl compound is illustrated here, this series of steps and reagents may be used to make other substituted-w-phenylaliphatic groups denoted by R. The starting material, the benzaldehydes, are commercially available or can be readily made by known methods.

To make the acid, first an alkylsilazide is added to an inert solvent under an inert atmosphere. Then the phosphonium salt is added. This addition can be done at room temperature or thereabouts. After a brief period of mixing, this mixture is usually a suspension, the benzaldehyde is added slowly at about room temperature. A slight molar excess of the phosphonium salt is employed. After an additional brief period of stirring at about room temperature, the reaction is quenched with water. The solution is acidified and the acid extracted with a suitable organic solvent. Further separatory and purification procedures may be employed as desired.

The alcohol is made by reducing the acid using a reducing agent. Lithium aluminum hydride or similar reducing agents may be employed, and conditions may be varied as needed to effect the reduction.

The tosylate is prepared in an inert solvent employing a base such as pyridine. Suitable conditions include carrying out the reaction at room temperature or thereabouts for a period of 1 to 5 hours. Other leaving groups similar in function to the tosylate may be prepared and will be useful as a means for forming the R moiety.

These procedures can be used to make the full spectrum of radicals represented by R where it has a terminal phenyl group, including the substituted phenylaliphatic radicals.

Benzyl mercaptans, or analogous compounds where m is 1 or greater, are commercially available or may be made by the process of Scheme III.

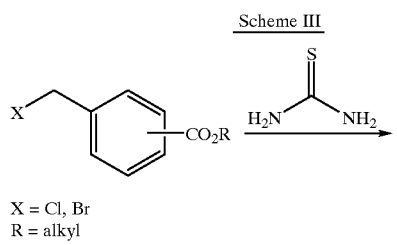

X = Cl, Br
R = alkyl

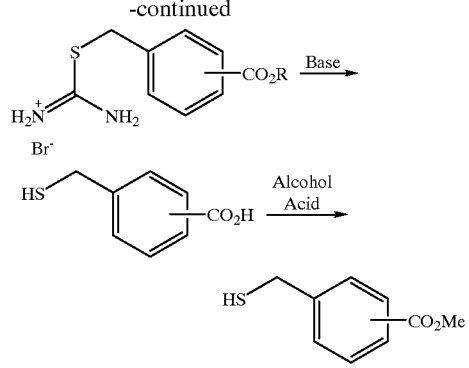

Starting material, the haloalkylbenzoates, are commercially available or can be made by methods known in the art. Thiourea is added to a solution of haloalkylbenzoate at ambient temperature or thereabouts. Any appropriate solvent may be used, acetone for example. A precipitate of the thiouronium salts should form under these conditions. The precipitate is collected and dissolved in water and the pH adjusted to about 10.5 with a base, for example a solution of NaOH. Refluxing is then commenced for between 1 and 4 hours. Product, as the free acid, is then recovered by some other separatory and purification means. Esterification is then carried out by mixing the acid with an alcohol, bubbling HCl through the solution, and letting sit the resulting solution for a time not more than several days; two days usually is sufficient to effect the reaction.

Compounds of formula I where Z is oxygen can be made by the sequence of steps given in Scheme IV.

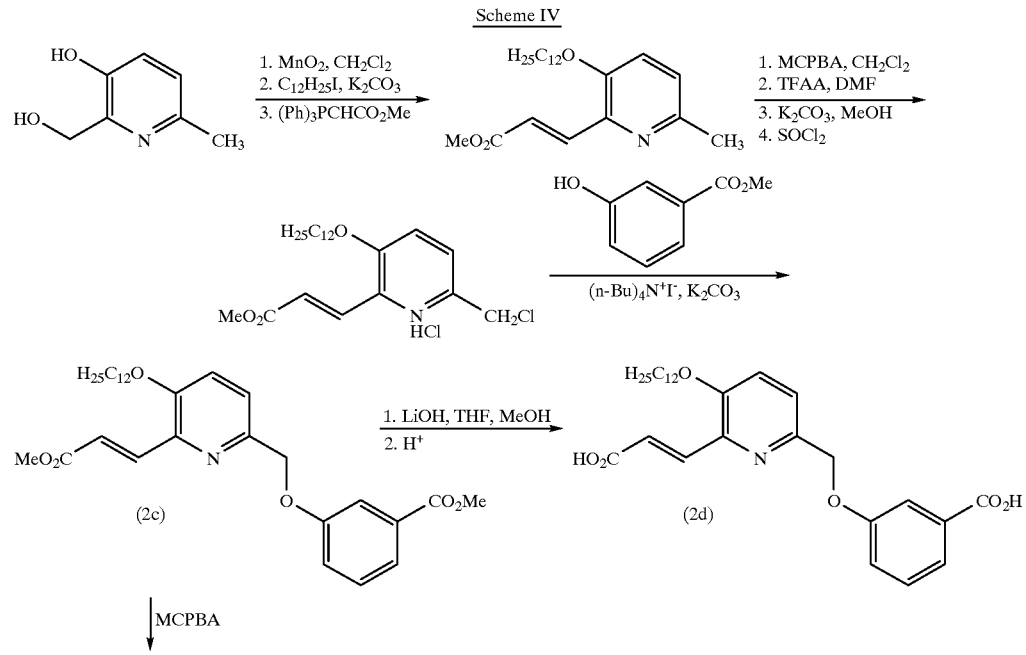

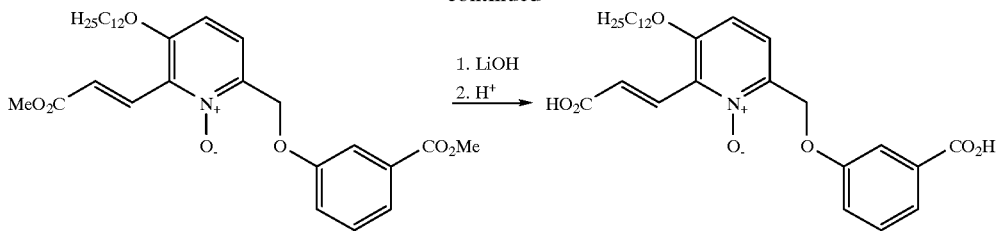

The starting material is available from Aldrich. It is treated with a mild oxidizing agent such as MnO₂ to oxidize the 2-hydroxyethyl group to the corresponding aldehyde. The R group is then formed. In this case an ether is prepared under basic conditions using an a-halo intermediate. A tosylate made as per Scheme III, can also be used in this step. Introducing the acid function at position 2 is accomplished by means of a triphenylphosphoranylidene reagent. The acetate form is illustrated here but other similar reagents could be used. The N-oxide is then formed by means of a peroxy acid. Trifluoroacetic anhydride is used to oxidize the 6-position methyl group. This hydroxymethyl group is then converted to the corresponding halide, (in the hydrohalide form) in this case the chloride, by means of thionyl chloride. An alkyl hydroxybenzoate is then reacted with the 6-chloromethyl compound in the presence of tetrabutylammonium iodide and a weak base. The resulting diester can be hydrolyzed to the salt or, further, acidified to give the free acid. An oxidant can be used to regenerate the N-oxide which can then be treated with base to hydrolyze the esters. Esters can be converted to salts, the free acids and other derivatives. Catalytic hydrogenation can be used to reduce the double bond in the R₁ group described here.

Scheme V illustrates a method for making compounds where Z is a S and m is 0.

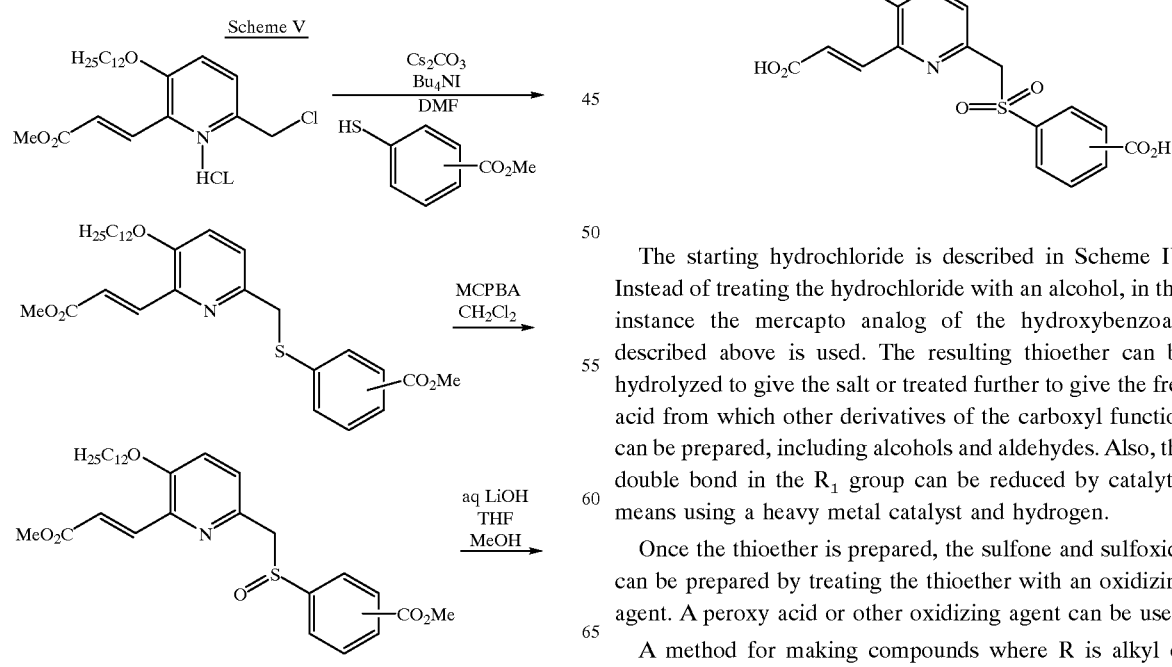

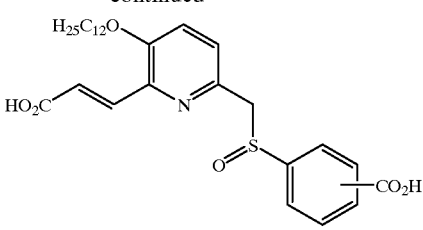

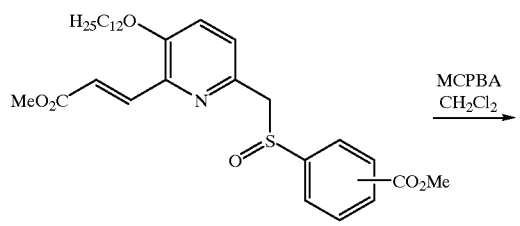

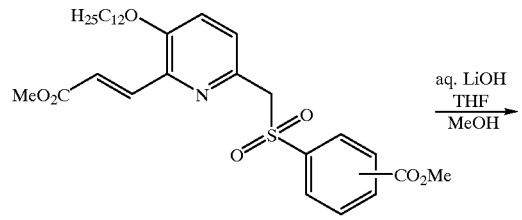

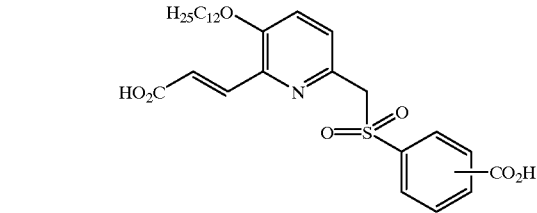

The starting hydrochloride is described in Scheme IV. Instead of treating the hydrochloride with an alcohol, in this instance the mercapto analog of the hydroxybenzoate described above is used. The resulting thioether can be hydrolyzed to give the salt or treated further to give the free acid from which other derivatives of the carboxyl function can be prepared, including alcohols and aldehydes. Also, the double bond in the R₁ group can be reduced by catalytic means using a heavy metal catalyst and hydrogen.

Once the thioether is prepared, the sulfone and sulfoxide can be prepared by treating the thioether with an oxidizing agent. A peroxy acid or other oxidizing agent can be used.

A method for making compounds where R is alkyl or substituted alkyl is given in Scheme VI

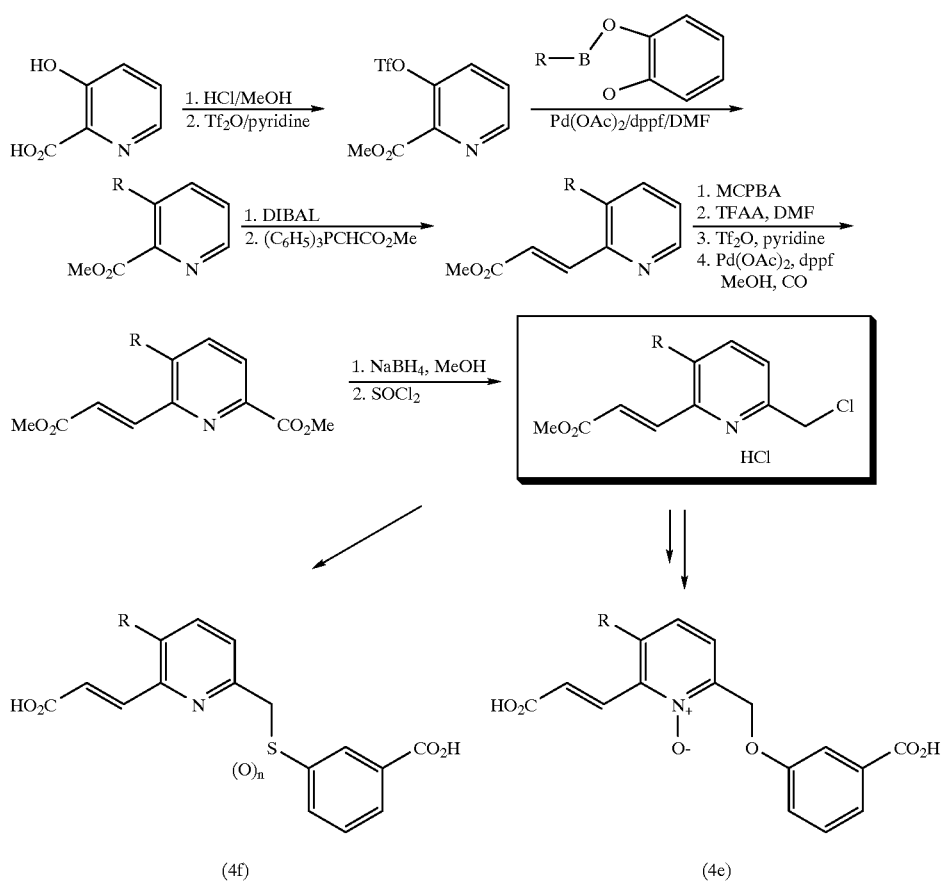

Scheme VI

In this Scheme, 2-hydroxypicolinic acid is converted to the alkyl ester using the corresponding alcohol and an acid to catalyze the reaction. The hydroxyl group is then converted to the trifluoromethylsulfonate by means of trifluoromethanesulfonic anhydride and a base, e.g. pyridine. The lipid tail is attached using the appropriate alkyl catechol boronate under palladium coupling conditions. For example, 1-iododecene and catechol borane are reacted to form the alkyl catechol boronate. Then the alkylation reaction is effected using Pd(OAc)$_2$. The ester is reduced to the corresponding aldehyde with a hydride such as diisobutylaluminum hydride (DIBAL). A Wittig olefination is then carried out using, for example, methyl(triphenylphosphoranylidene) acetate. The resulting pyridyl methyl acrylate is then oxidized to the N-oxide with an oxidizing agent such as 3-chloroperoxybenzoic acid. This oxide is then rearranged to the 2-pyridone with trifluoroacetic anhydride. A trifluoromethylsulfonate is then formed using trifluoromethanesulfonic anhydride and pyridine. Carbomethylation is then effected by means of Pd(OAc)$_2$, a simple alcohol, and carbon monoxide. Selectively reducing the pyridyl-ester (using a hydride such as NaBH$_4$ in a low molecular weight alcohol) yields the 2-(hydroxymethyl)-pyridine. This compound is treated with thionyl chloride to form the 6-chloromethyl compound. This intermediate is transformed to the ethers or thioether of formula I in the same manner as is illustrated in Schemes IV–VI.

Pharmaceutical compositions of the present invention comprise a pharmaceutical carrier or diluent and some amount of a compound of the formula (I). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For parenteral administration the pharmaceutical composition will be in the form of a sterile injectable liquid such as an ampule or an aqueous or non-aqueous liquid suspension.

For topical administration the pharmaceutical composition will be in the form of a cream, ointment, liniment, lotion, pastes, and drops suitable for administration to the eye, ear, or nose.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water, for non-aqueous systems, ethanol, glycerin, propylene glycol, corn oil, cottonseed oil, peanut oil, sesame oil, liquid parafins and mixtures thereof with water, for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

Formulations for treating atopic or contact dermatitis can take the form of oral or topical preparations. Topically applied formulations are preferred. Ointments, creams, liniments, lotions, pastes and similar preparations are examples of preferred topical formulations. Aerosols may also be used. These dosage forms will contain between 0.01 and 5 percent by weight of the active ingredient.

Usually a compound of formula I is administered, that is applied, to a subject in a composition comprising a nontoxic amount sufficient to produce an inhibition of the symptoms of a disease state. When administered orally, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg. When a topical formulation is used, the amount applied will depend on the size of the affected area and the severity and progress of the disease, i.e., atopic dermatitis or contact dermatitis.

This disclosure related to a method for treating atopic dermatitis, or contact dermatitis.

Atopic dermatitis is a chronic eruption occurring in adolescents and adults. It's origin is not known although allergic, hereditary and psychogenic factor appears to be involved. The lesions occur chiefly on the flural surfaces of the knees and elbows, but may involve other areas. They are marked by lichenfication, excoriations, and crusting. In infants and young children the condition is sometimes called infantile eczema or Besnier's prurigo. It is also called allergic dermatitis, flexural eczema, and disseminated neurodermatitis.

Contact dermatitis is an acute allergic inflammation of the skin caused by contact with various substances of a chemical, animal, or vegetable nature to which delayed hypersensitivity has been acquired; when severe, it is called dermatitis venata.

Treatment may be carried out in dosage units at suitable intervals or in single doses as needed. Usually this method will be practiced when relief of symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the condition or disease being treated, and so forth.

No toxicity is expected to be encountered when the method of this invention is carried out in conformity with the instructions set forth herein and good medical practice.

Specific Embodiments

The following examples are given to illustrate how to make and use the compounds of this invention. These Examples are just that, examples, and are not intended to circumscribe or otherwise limit the scope of this invention. Reference is made to the claims for defining what is reserved to the inventors by this document.

The compounds of this invention can be made by the processes set out in copending U.S. applications U.S. Ser. No. 08/211,063 filed 18 Jul. 1994 (arising from PCT application PCT/US92/07466 published as WO 93/06085) and U.S. Ser. No. 08/356,358 filed 19 Dec. 1994 (arising from PCT/US93/06234 published as WO 94/00437).

EXAMPLE 1

Topical formulations

Formulations for pharmaceutical use incorporating compounds of the present invention can be prepared in various forms and with numerous excipients. Means for making various formulations can be found in standard texts such as Remington's Pharmaceutical Sciences, and similar publications and compendia. Specific examples of formulations are given below.

Ointments

Hydrophyllic Petrolatum

| Ingredients | Amount (% Weight/weight) |
| --- | --- |
| Cholesterol | 30.0 g |
| Stearyl Alcohol | 30.0 g |
| White Wax | 78.0 g |
| Active Ingredient | 2.0 g |
| White Petolatum | 860.0 g |

The stearyl alcohol, white wax and white petrolatum are melted together (steam bath for example) and cholesterol and the active ingredient are added. Stirring is commenced and continued until the solids disappear. The source of heat is removed and the mix allowed to congeal and packaged in metal or plastic tubes.

Emulsion Ointment

| Ingredients | Amount (% W/W) |
| --- | --- |
| Methylparaben | 0.25 g |
| Propylparaben | 0.15 |
| Sodium Lauryl Sulfate | 10.0 g |
| Active Ingredient | 5.0 g |
| Propylene Glycol | 120.0 g |
| Stearyl Alcohol | 250.0 g |
| White Petrolatum | 250.0 g |
| Purified Water | QS to 1000.0 g |

The stearyl alcohol and white petrolatum are combined over heat. Other ingredients are dissolved in water, then this solution is added to the warm (ca 50 to 100° C.) alcohol/petrolatum mixture and stirred until the mixture congeals. It can then be packed in tubes or another appropriate package form.

What is claimed is:

1. A method for treating atopic dermatitis or contact dermatitis in a mammal which process comprises administering to a mammal suffering from either disease a therapeutically effective amount of at least one compound of formula I

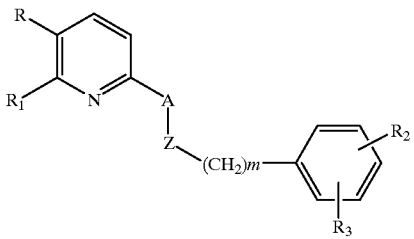

or an N-oxide, or a pharmaceutically acceptable salt thereof, where

A is $CH_2$ and Z is $S(O)_q$ where q is 0, 1 or 2; or O; or m is 0–5;

R is $C_1$ to $C_{20}$-aliphatic, unsubstituted or substituted phenyl $C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O-, or R is unsubstituted or substituted phenyl $C_1$ to $C_{10}$-aliphatic-O- where substituted phenyl has one or more radicals selected from the group consisting of lower alkoxy, lower alkyl, trihalomethyl, and halo;

$R_1$ is —($C_1$ to $C_5$ aliphatic)$R_4$, —($C_1$ to $C_5$ aliphatic)CHO, —($C_1$ to $C_5$ aliphatic)$CH_2OR_8$, —$R_4$, —$CH_2OH$, or CHO;

$R_2$ is H, halo, lower alkyl, lower alkoxy, —CN, —$(CH_2)_n R_4$, —$CH(NH_2)(R_4)$, or —$(CH_2)_n R_9$ where n is 0–3 and where $R_9$ is —$N(R_7)_2$, where each $R_7$ is independently H, or an aliphatic hydrocarbon group of 1 to 10 carbon atoms, or acyl of 1–6 carbon atoms, or a cycloalkyl—$(CH_2)_n$— group of 4 to 10 carbons where n is 0–3, or both $R_7$ groups form a ring which includes the nitrogen and having 4 to 6 carbons; or $R_3$ is hydrogen, lower alkyl, lower alkoxy, halo, —CH, $R_4$, $NHCONH_2$, or OH;

each $R_4$ group is independently —$COR_5$ where $R_5$ is —OH, or —OX where X is a pharmaceutically acceptable cation, or $R_5$ is —$N(R_7)_2$ where each $R_7$ is independently H, or an aliphatic group of 1 to 10 carbon atoms, or a cycloalkyl—$(CH_2)_n$— group of 4 to 10 carbons where n is 0–3, or both $R_7$ groups form a ring having 4 to 6 carbons, or $R_4$ is a sulfonamide, or an amide, or tetrazol-5-yl; and $R_8$ is hydrogen, $C_1$ to $C_6$ alkyl, or $C_1$ to $C_6$-acyl.

2. The method of claim 1 where, in formula 1, Z is $S(O)_q$ and m is 0 or 1.

3. The method of claim 2 where in formula 1, R is alkoxy of 8 to 15 carbon atoms or unsubstituted or substituted pheny-$C_1$ to $C_{10}$-alkyl-O- where substituted phenyl is substituted with fluoro, trifluoromethyl or methoxy and $R_1$ is $R_4CH=CH$— or $R_4CH_2CH_2$—.

4. The method of claim 3 where in formula 1 q is 0 and m is 0.

5. The method of claim 2 which uses a compound of formula 1 where R is unsubstituted or substituted phenyl-$C_2$ to $C_{10}$ alkoxy.

6. The method of claim 2 which uses a compound of formula 1 which is (E)-3-[3-[2-phenethyloxy]-6-[(2,6-dichlorophenylsulfinyl)methyl]-2-pyridinyl]-2-propenoic acid or a pharmaceutically acceptable salt thereof.

* * * * *